United States Patent [19]
Cumming

[11] Patent Number: 5,578,042
[45] Date of Patent: Nov. 26, 1996

[54] OPHTHALMIC KIT AND METHOD FOR LENS INSERTION

[76] Inventor: J. Stuart Cumming, 1211 W. LaPalma Ave., #201, Anaheim, Calif. 92801

[21] Appl. No.: 213,235

[22] Filed: Mar. 14, 1994

[51] Int. Cl.$^6$ .............................. A61B 19/00; A61F 9/00
[52] U.S. Cl. ........................................ 606/107; 128/898
[58] Field of Search ........................... 606/1, 107; 623/4, 623/6; 128/898

[56] References Cited

U.S. PATENT DOCUMENTS

| | | | |
|---|---|---|---|
| 4,715,373 | 12/1987 | Mazzocco et al. | 606/107 |
| 4,763,650 | 8/1988 | Hauser | 606/107 |
| 4,834,094 | 5/1989 | Patton et al. | 606/107 |
| 4,862,885 | 9/1989 | Cumming | 606/107 |
| 4,976,716 | 12/1990 | Cumming | 606/107 |

FOREIGN PATENT DOCUMENTS

| 5103808 | 4/1993 | Japan | 606/107 |
|---|---|---|---|

Primary Examiner—Glenn Dawson
Attorney, Agent, or Firm—Boniard I. Brown

[57] ABSTRACT

An ophthalmic kit contains a foldable intraocular lens and a disposable lens insertion device in a sterile condition with the lens positioned in its normal unfolded configuration between open jaws of the insertion device until needed for lens implantation. When needed for lens implantation, the jaws of the insertion device are closed about the lens to fold the lens to a compact folded configuration while the insertion device and lens are on the tray. The insertion device is then placed in a reusable handle to form an ophthalmic instrument which holds the jaws closed with an anterior tip portion of the insertion device projecting beyond the anterior end of the handle for insertion into a patient's eye through an incision, and plunger is moved forwardly through the handle and insertion device to eject the folded lens into the patient's eye.

54 Claims, 6 Drawing Sheets

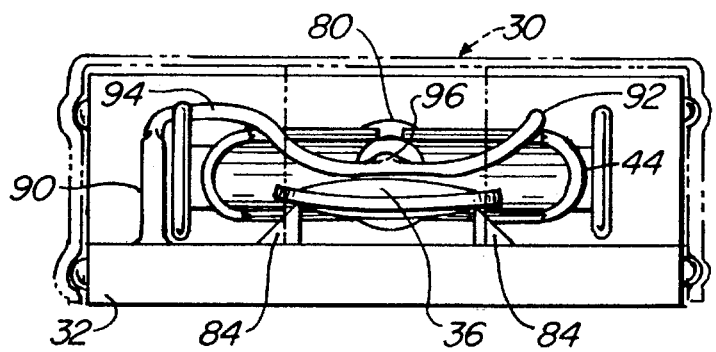
FIG.—2A
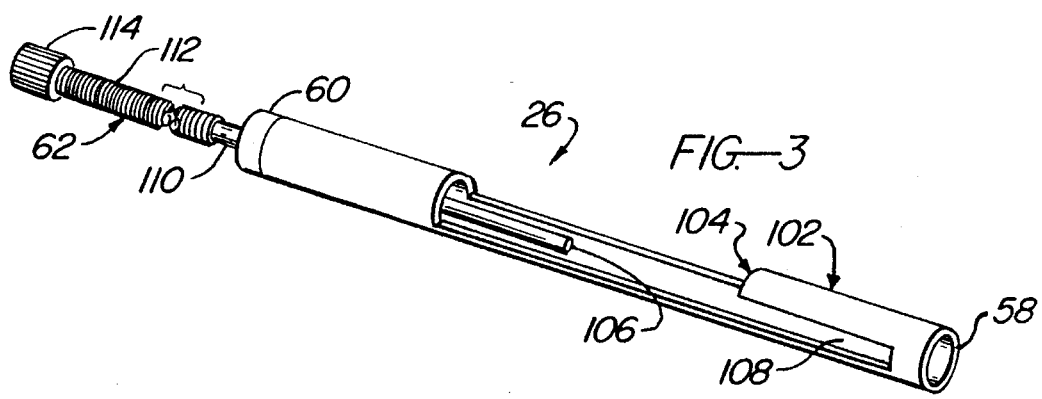
FIG.—3
FIG.—3A
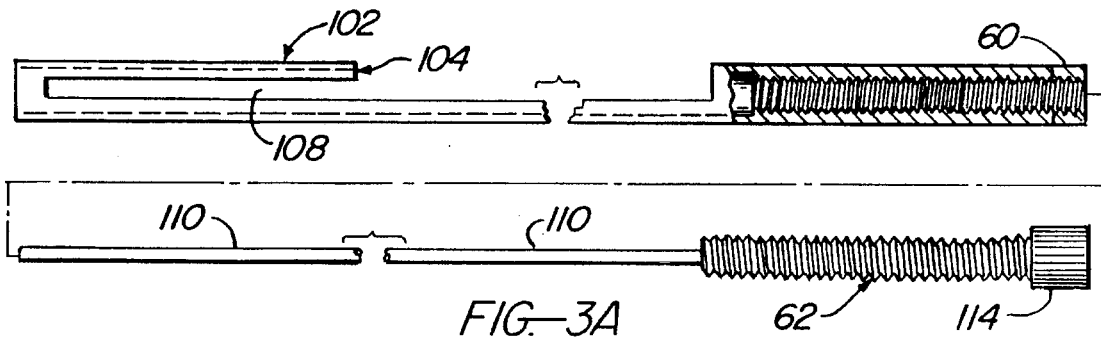
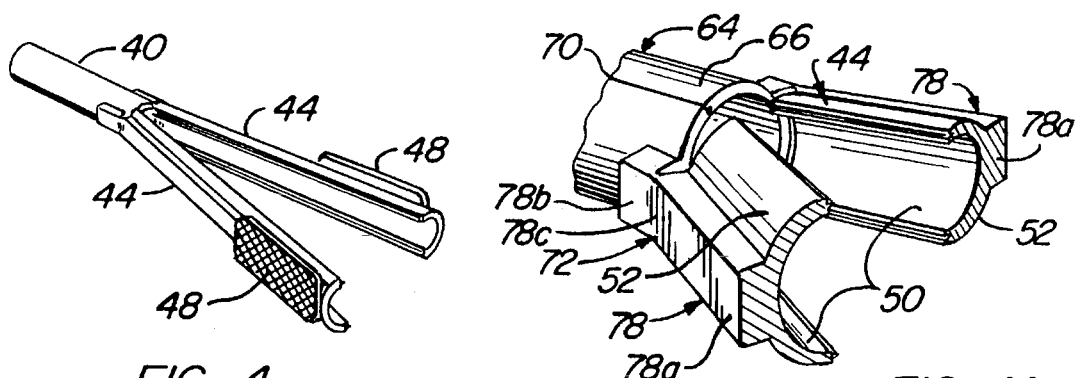
FIG.—4
FIG.—4A

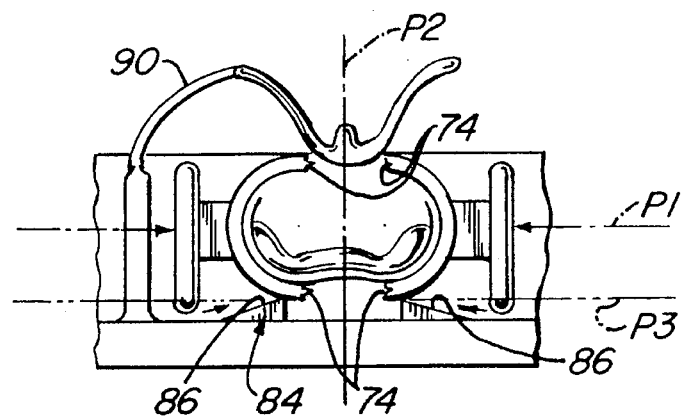
FIG.-8
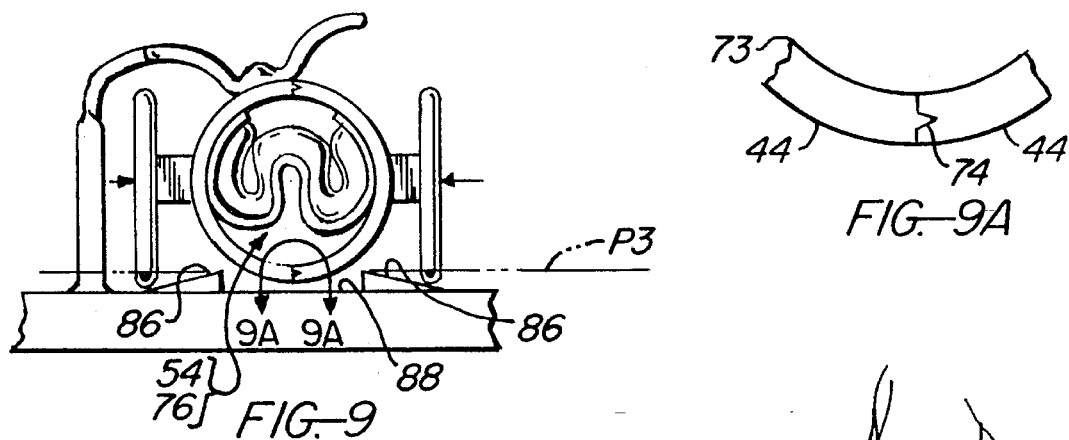
FIG.-9
FIG.-9A
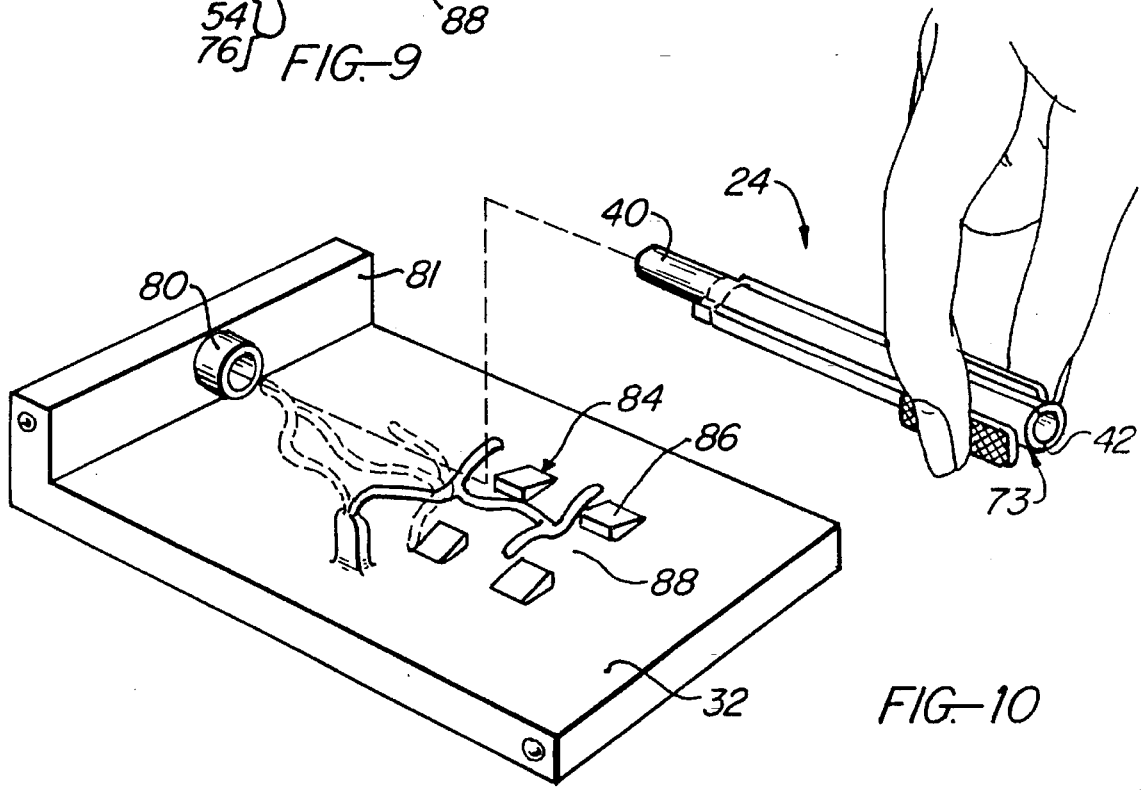
FIG.-10

OPHTHALMIC KIT AND METHOD FOR LENS INSERTION

BACKGROUND OF THE INVENTION

1. Field of the Invention

This invention relates generally to the field of ophthalmology and more particularly to a novel ophthalmic kit and ophthalmic method and instrument for use in implanting a foldable intraocular lens in a patient's eye,

2. Discussion of the Prior Art

The human eye has a crystalline lens situated behind the iris including an outer capsule attached by zonules to the ciliary muscle of the eye and a crystalline matrix filling the capsule. The lens capsule has anterior and posterior membrane-like walls referred to as anterior and posterior capsules, respectively. In a normal eye, the lens is optically clear. Light rays entering the eye through its cornea and iris pass through the lens to the retina of the eye, and the lens is automatically shaped by brain control of the ciliary muscle to focus these incoming light rays on the retina.

The human eye is subject to a variety of abnormal conditions that degrade or totally destroy proper optical functioning of the eye. One of the more common of these conditions is known as a cataract and involves clouding of the crystalline lens matrix which obstructs or blocks passage of light rays through the lens to the retina. Simply stated, the ophthalmic procedure for curing a cataract involves extraction of the cataractous natural lens through an incision in the eye and implantation of an artificial intraocular lens in the eye through the incision.

In the early days of such cataract surgery, the entire cataractous natural lens was removed by a surgical procedure known as intra-capsular lens extraction. While this procedure is occasionally used today in certain circumstances, it has many disadvantages among the more serious of which is the need to make a relatively large incision in the eye to permit removal of the natural lens through the incision.

These disadvantages of intra-capsular lens extraction led to the development in the 1970's of an improved procedure for removing a cataractous natural lens. This improved procedure, known as extra-capsular extraction, involves removal of only the anterior capsule or a central portion of the anterior capsule of the natural lens, phacoemulsification of the cataractous natural lens matrix, and aspiration of the emulsified matrix. This extra-capsular extraction procedure with phacoemulsification requires only a relatively small incision on the order of 3 mm in length and thereby reduces or eliminates many of the risks associated with intra-capsular lens extraction.

It was not until the development of the foldable intraocular lens in 1986, however, that the small incision advantage of extra-capsular lens extraction with phacoemulsification could be utilized. This was due to the fact that up until 1986, the only available intraocular lenses were herd lenses which required an incision on the order of 6–8 mm in length for insertion into the eye. Accordingly, even though the natural lens was extracted through a 3 mm incision, the surgeon had to enlarge the incision to 6–8 mm in order to insert the hard intraocular lens into the eye.

A foldable intraocular lens has a normal unfolded lens configuration in which the lens is conditioned to perform its intraocular lens function. The lens is foldable to a compact folded configuration for insertion into the eye through a small incision, such as the 3 mm incision required by extracapsular lens extraction with phacoemulsification. In its folded configuration, the lens stores elastic strain energy which unfolds the lens to its normal lens configuration when it is released within the eye.

A variety of foldable intraocular lenses and instruments for inserting such lenses into the eye have been developed over the period from 1986 to the present. Among the patents disclosing such lenses and instruments are the following:

U.S. Pat. No. 4,575,998 dated Mar. 4, 1986, to Mazzocco discloses (FIGS. 31–61) a variety of foldable intraocular lenses and instruments for inserting the lenses into the eye including instruments having a pair of opposing jaws which are closed about a foldable lens (FIGS. 52, 54).

U.S. Pat. No. 4,681,102 dated Jul. 21, 1987, to Bartell discloses a foldable lens insertion instrument including a load chamber which is closable longitudinally about a foldable intraocular lens to fold the lens and insertable into a lens insertion device including a plunger movable forwardly through the insertion device and load chamber to push the folded lens through the anterior tip of the device into the eye.

U.S. Pat. No. 4,715,373 dated Dec. 29, 1987, to Mazzocco et al discloses an instrument having a pair of jaws for gripping a foldable intraocular lens in its folded configuration, a sleeve for surrounding the jaws to hold them in their closed positions, and means for releasing the folded lens from the instrument into the eye.

U.S. Pat. No. 4,765,329 dated Aug. 23, 1988, to Cumming discloses a sterile ophthalmic package or kit containing a tube for holding a foldable intraocular lens and having a slender anterior tip for insertion into the eye, and a probe for pushing the lens from the tube, through the tip, into the eye.

U.S. Pat. No. 4,862,885 dated Sep. 5, 1989, to Cumming discloses a sterile ophthalmic package or kit including a tray holding a disposable lens insertion device having a pair of open lens gripping jaws straddling an unfolded deformable intraocular lens supported on the tray with the length of the lens extending lengthwise of the jaws, means on the tray for closing the jaws about the lens to fold and grip the lens in its folded configuration, and a handle including means for holding the jaws closed and pushing the folded lens from the jaws into the eye following removal of the instrument and lens from the tray and insertion of the jaws of the insertion device into the eye.

U.S. Pat. No. 4,934,363 dated Jun. 19, 1990, to Smith discloses an ophthalmic instrument having a disposable insertion device including a tube insertable into the eye and containing a movable lens holder, a reusable handle removably mounting the insertion device including means for moving the lens holder back and forth in the tube of the insertion device to first draw a foldable lens into the tube and thereby fold the lens and thereafter eject the folded lens from the tube into the eye.

U.S. Pat. No. 4,976,716 dated Dec. 11, 1990, to Cumming discloses a sterile ophthalmic package or kit including a tray holding a disposable lens insertion device having a pair of open lens gripping jaws straddling an unfolded deformable intraocular lens supported on the tray with the length of the lens extending lengthwise of the jaws, means on the tray for closing the jaws about the lens to fold and grip the lens in its folded configuration, and a reusable handle for holding the jaws closed and including a plunger for pushing the folded lens from the insertion device into the eye following removal of the instrument and lens from the tray and insertion of the jaws of the insertion device into the eye.

BRIEF DESCRIPTION OF THE INVENTION

This invention provides an improved ophthalmic instrument package or kit and an improved ophthalmic instrument and method for implantation of a foldable intraocular lens in a patient's eye. The improved instrument of the invention includes a lens insertion device, which may be disposable, and a handle, which may be reusable, for removably receiving the insertion device. The lens insertion device has a slender anterior end for insertion into a patient's eye through a small incision in the eye and a pair of lens gripping jaws. These jaws are movable between open and closed positions and compress the lens from its anterior to its posterior end. When closed, the jaws form a passage opening through the anterior and posterior ends of the device. The instrument handle has anterior and posterior ends and removably receives the insertion device with its jaws closed and in an assembled position wherein the anterior end of the insertion device projects beyond the anterior end of the handle to permit insertion of the anterior end of the insertion device into the patient's eye. Included in the handle are lens ejection means for moving the folded lens forwardly through the passage in the lens insertion device and then ejecting the lens from the insertion device into a patient's eye through the anterior end of the device.

The ophthalmic kit of the invention comprises a sterile instrument holder including a tray for holding the foldable lens and the lens insertion device in a sterile condition until needed for lens implantation. The insertion device and lens are supported on the tray with the jaws of the device open and straddling the lens in its normal unfolded configuration. Mounted directly on the insertion device at its posterior part are means for closing the jaws from front to back about the unfolded lens to fold the lens to its folded configuration and confine or grip the folded lens within the passage formed by the closed jaws.

When the foldable intraocular lens is to be implanted in a patient's eye, a sterile instrument handle and the sterile ophthalmic kit containing the lens insertion device and unfolded lens are supplied to the surgeon in the operating room. The kit is opened in the operating room, and the jaws of the lens insertion device are closed about the lens compressing it from front to back to fold and grip the lens between the jaws while the insertion device and lens are still on the holder tray. The insertion device is then removed from the tray along with the now folded lens confined and gripped between the closed jaws and inserted into the instrument handle to form the ophthalmic instrument of the invention. The projecting anterior end of the insertion device is now inserted into the patient's eye through a small incision in the eye, and the lens ejection means of the handle is utilized to eject the folded lens through the insertion device into the eye. The lens unfolds to its normal configuration within the eye and is manipulated to its proper position in the eye by the surgeon. A major advantage of the invention resides in the fact that this entire lens implantation procedure occurs without any direct contact of a person with the lens and hence without any possibility of contamination of the lens by operating room personnel or any one else. In addition, because the lens is enclosed in the insertion device which is inserted into the eye through a small incision, the lens never comes into contact with the outside tissues of the eye, thus further reducing the risk of contamination.

The preferred lens insertion device of the invention is disposable and includes a tubular anterior nose section having a posterior end and a slender anterior tip portion. This anterior nose section contains a passage which opens through the tip portion and the posterior end of the section. The lens gripping jaws of the preferred lens insertion device are secured, preferably by hinges, to the posterior end of the anterior nose section at opposite sides of its passage. The passage formed by the jaws when closed, referred to herein as a jaw passage, is coaxial with and opens forwardly to the nose section passage, and the two passages form a lens insertion passage extending longitudinally through and opening through the anterior and posterior ends of the insertion device. Mounted on the outer sides of the jaws are finger pads which may be gripped between the thumb and forefinger to squeeze the jaws closed and then remove the insertion device from the tray and insert the device into the instrument handle.

The preferred instrument handle of the invention reusable and comprises a tube having open anterior and posterior ends and a sidewall opening. This sidewall opening includes posterior portion through which the lens insertion device insertable into and removable from the handle and a pair of diametrically opposed longitudinal slots extending forwardly from the posterior portion. These slots receive projecting longitudinal ribs on the insertion device to orient the device relative to the handle in a position wherein the anterior tip portion of the insertion device projects sufficiently beyond the anterior end of the handle for insertion into a patient's eye. Threaded in the posterior end of the handle is a lens ejection plunger which is movable forwardly through the handle and lens insertion passages of the lens insertion device to push the folded lens forwardly through the passages into the patient's eye.

BRIEF DESCRIPTION OF THE DRAWINGS

FIG. 2A is a view looking in the direction of the arrows on line 2A—2A in FIG. 2;

FIG. 3 is a perspective view of a reusable handle for holding the lens insertion device and lens of FIG. 1 during implantation of the lens in a patient's eye;

FIG. 3A is an exploded side elevational view of the handle in FIG. 3;

FIG. 4 is a perspective view of the lens insertion device in FIG. 1 showing lens gripping jaws of the device in their normal open positions;

FIG. 4A is an enlarged fragmentary perspective view of a portion of the device of FIG. 4, showing details of hinge feature:

FIG. 8 is a view looking in the direction of the arrows on line 8—8 in FIG. 7 after the jaws of the insertion device have been partially closed and illustrating the manner in which the lens is folded between the closing jaws;

FIG. 9 is a view similar to FIG. 8 following complete closure of the jaws illustrating the lens in its fully folded configuration:

FIG. 9A is a fragmentary view taken at arrow 9A—9A in FIG. 9:

FIG. 10 is a view similar to FIG. 7 illustrating the manner in which the lens insertion device and folded lens are removed from the instrument tray for insertion into the handle of FIG. 3;

DESCRIPTION OF THE PREFERRED EMBODIMENT

Figure 1:
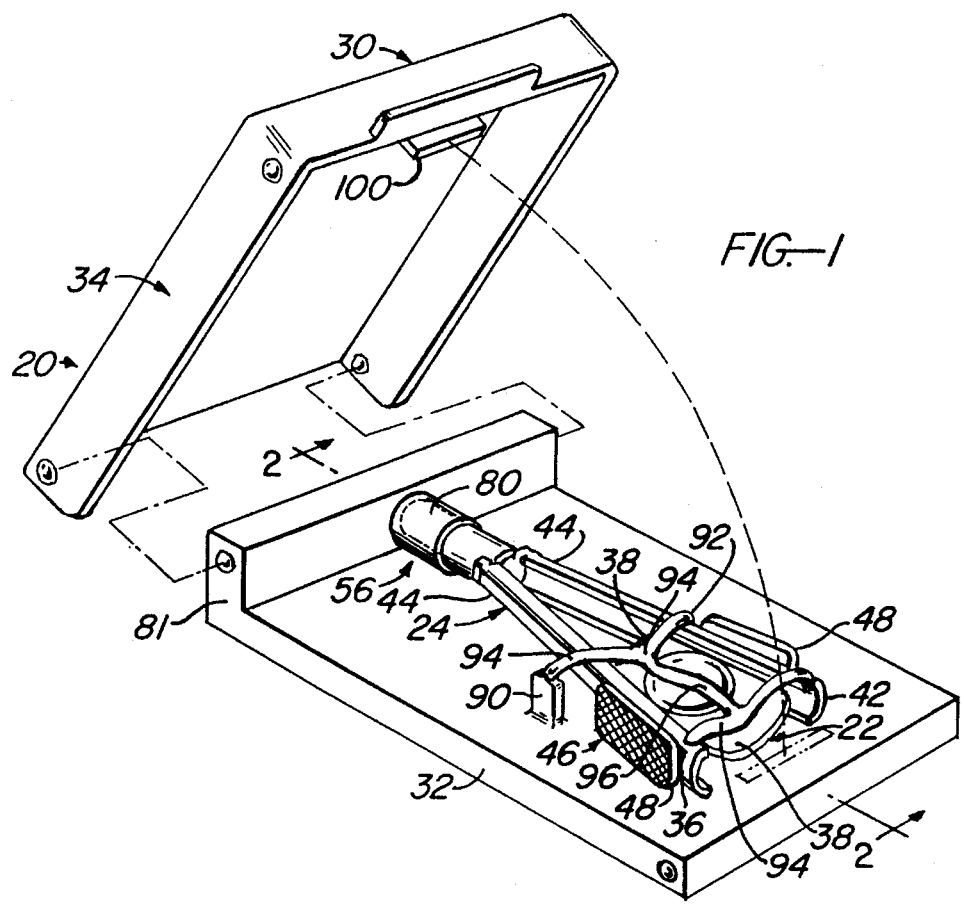
FIG. 1 is a perspective view of an ophthalmic kit according to the invention including a foldable intraocular lens, a disposable lens insertion device, and an instrument holder in the form of a handling or shipping case having an instrument tray for holding the insertion device and lens in a sterile condition until needed for lens implantation.

Referring now to these drawings, there is illustrated an ophthalmic kit 20 according to the invention including a foldable intraocular lens 22, a lens insertion device 24 to be assembled with a handle 26 to form an ophthalmic instrument 28 according to the invention for inserting the lens into a patient's eye, and a normally sealed instrument holder 30 for storing the insertion device and lens in a sterile condition until needed for lens implantation. The illustrated instrument holder 30 is a handling or shipping case including a normally bottom base or tray 32 and a hinged cover 34 which can be opened or removed to uncover the tray 32.

The foldable intraocular lens 22 is conventional and hence need not be described in elaborate detail. Suffice it to say that the lens has a central optic 36 and diametrically opposed haptics 38. The particular lens illustrated is a plate haptic lens. It will become evident as the description proceeds, however, that the invention may be utilized with other foldable intraocular lenses. The lens is composed of deformable material which permits the lens to be folded without damage. The lens has a normal generally flat unfolded lens configuration in which the lens is conditioned to function as an intraocular lens replacement for the natural lens of the eye. The lens is foldable to a relatively compact folded configuration in which the lens is conditioned for insertion into the eye through a relatively small incision on the order of 3 mm in length. When thus folded, the lens stores elastic strain energy which unfolds the lens to its normal lens configuration when it is released in the eye.

In the ensuing description, reference is made to the longitudinal axis of the lens 22. This is an axis transverse to and intersecting the optic axis of the lens optic 36 and located in a plane containing the optic axis and the longitudinal centerlines of the lens haptics 38.

Figure 5:
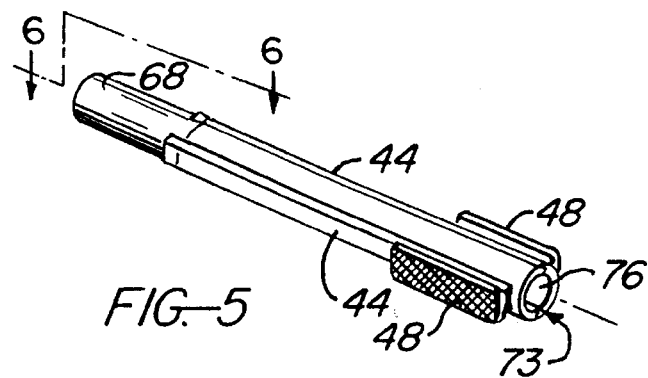
FIG. 5 is a view similar to FIG. 4 showing the jaws of the insertion device in their closed positions.

The lens insertion device 24 has a normally anterior end 40 insertable into a patient's eye through an incision in the eye and an opposite posterior end 42. The insertion device includes a pair of lens gripping jaws 44 which extend longitudinally of the insertion device and are supported at one end on the insertion device for movement of the opposite free ends of the jaws away from one another to their open positions of FIGS. 1, 2, 4, and 4A and toward one another to their closed positions of FIGS. 5, 9 and 10. Mounted directly on the insertion device 24, and more specifically on the jaws 44, are jaw closing means 46 engageable by a person's fingers for moving the jaws from their open positions to their closed positions.

Figure 6:
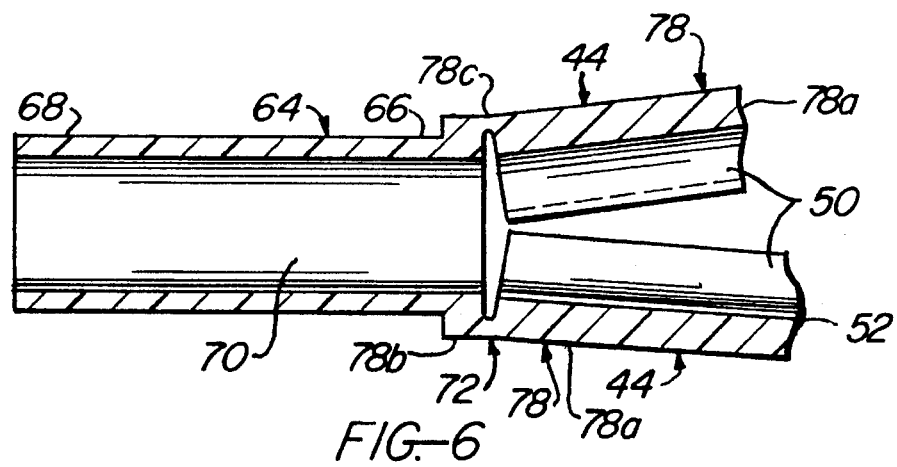
FIG. 6 is a section taken on line 6—6 in FIG. 5, showing hinge features of the device with the jaws in open positions.
Figure 7:
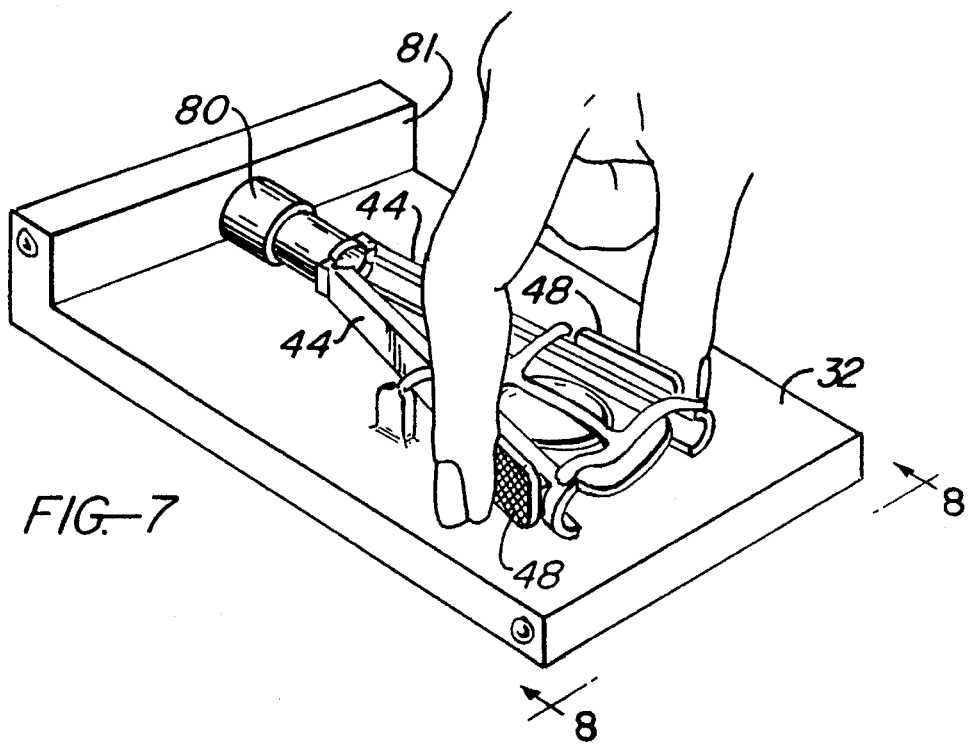
FIG. 7 is a view similar to FIG. 1 illustrating the manner in which the jaws of the insertion device are gripped to close the jaws about and fold the lens while the insertion device and lens are still on the tray of the instrument holder.

The illustrated jaw closing means 46 comprise finger pads 48 on the jaws 44 which may be gripped between the thumb and forefinger, as shown in FIG. 7, to close the jaws. Jaws 44 have confronting inner longitudinal sides 50 and opposite outer longitudinal sides 52. The finger pads 48 are mounted on the outer sides 52 of the jaws adjacent their free ends. The confronting inner sides 50 of the jaws are concave and form a passage 54 (FIGS. 6 and 9), hereafter referred to as a jaw passage, which opens through the anterior and posterior ends 40, 42 of the insertion device when the jaws are closed.

Figure 2:
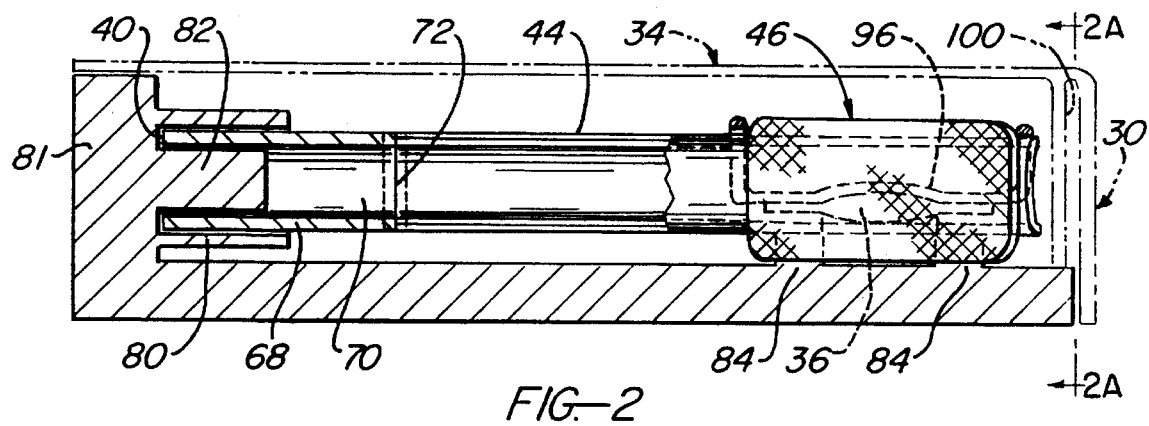
FIG. 2 is a section taken on line 2—2 in FIG. 1.

The instrument tray 32 includes supporting means 56 for removably supporting the insertion device 24 and the foldable intraocular lens 22 on the tray in their storage positions of FIGS. 1 and 2. In these storage positions, the jaws 44 of the insertion device 24 occupy their wide open positions, the lens 22 is positioned between the open jaws with the lens in its normal unfolded configuration, and the finger pads 48 are accessible to be squeezed to close the jaws about the lens while the insertion device and lens remain on the tray, as shown in FIG. 7. This closure of the jaws folds the lens to its compact folded configuration of FIG. 9 within the jaw passage 54. The insertion device 24 is then removable from the tray, for assembly with the handle 26 to form the ophthalmic instrument 28, by continued gripping of the finger pads 48 between the fingers to hold the jaws 44 closed about the folded lens 22, as shown in FIG. 10.

Handle 26 has normally anterior and posterior ends 58, 60, respectively, and is adapted to receive the insertion device 24 immediately following its removal from the tray 32 with its jaws 44 closed and enclosing folded lens 22, as illustrated in FIG. 10. The handle is constructed and arranged to receive the insertion device in the assembled position of FIGS. 11–14. In this assembled position, the handle holds the jaws 44 of the insertion device closed with the lens 22 gripped in its folded configuration within the jaw passage 54 and with the anterior end 40 of the insertion device projecting beyond the anterior end 58 of the handle for insertion into the patient's eye. The handle 26 includes lens ejection means 62 for moving the folded lens 22 forwardly through the passage 54 to eject the lens from the ophthalmic instrument 28 into the patient's eye through the projecting anterior end 40 of the insertion device 24 in the manner explained later.

Referring now in more detail to the drawings, the illustrated and presently preferred lens insertion device 24 of the invention has a tubular anterior nose section 64 including a posterior portion 66 and an anterior tip portion 68. The anterior tip portion extends forwardly and is externally tapered radially inwardly to a relatively small tip diameter from the posterior portion 66 to the anterior end 40 of the insertion device. Extending longitudinally through and opening through the anterior and posterior ends of the nose section 64 is a passage 70 which is of the same diameter throughout its length. The lens gripping jaws 44 of the insertion device extend rearwardly from the posterior end of the nose section 64 and have anterior ends secured by hinges 72 to the posterior end of the nose section at diametrically opposite sides of the nose section passage 70. The jaws have posterior free ends which are movable toward and away from one another between the closed and open jaw positions mentioned earlier. Accordingly, the nose section 64 provides supporting means which supports the jaws 44 at their anterior ends for opening and closing movement of their posterior free ends.

The lens gripping jaws 44 are generally semicylindrical in shape and have concave surfaces at their confronting inner sides 50 which are generally cylindrically curved about axes extending lengthwise of the respective jaws. Accordingly, when the jaws 44 are closed, they form a generally cylindrical or oval tube 73. The jaw passage 54 formed by the closed jaws is generally circular or oval in cross-section and has a substantially uniform diameter along its entire length. This jaw passage is coaxial with and opens forwardly to the nose section passage 70. The jaw passage opens rearwardly through the posterior end 42 of the lens insertion device 24, that is through the posterior end of the tube 73 formed by the closed jaws. The confronting inner longitudinal edges of the jaws 44 have mating tongue and groove formations 74 which interengage when the jaws are closed to accurately coaxially align the jaws relative to one another in such a way that the jaws and the jaw passage 54 are coaxial with the longitudinal axis of the nose section 64 and nose section passage 70.

The outer diameter of the tube 73 formed by the closed jaws 44 substantially equals the outer diameter of the posterior end portion 66 of the insertion device nose section 64. Accordingly, when the jaws are closed, the lens insertion device 24 forms an essentially continuous tubular barrel which has a substantially uniform outside diameter along a major portion of its length from its posterior end 42 and which necks down at its anterior end to form the anterior tip portion 66 of the device. Similarly, the inner diameter of the jaw passage 54 substantially equals the inner diameter of the nose section passage 70. When the jaws are closed, therefore, the jaw passage 54 and nose section passage 70 form a continuous passage 76, hereafter referred to as a lens insertion passage, extending axially through and opening through the anterior and posterior ends 40, 42 of the lens insertion device 24. The anterior end portion of this lens insertion passage externally necks down smoothly to a relatively small uniform thin-walled anterior tip portion 68.

The hinges 72 of the lens gripping jaws 44 have parallel hinge axes located in a common plane transverse to the common longitudinal axis of the lens insertion device 24 and lens insertion passage 76. The jaws move or pivot between their open and closed positions parallel to a plane P1, hereafter referred to as a jaw plane, transverse to the hinge axes and containing the longitudinal axis of the insertion device nose section 64. Along the outer sides of the jaws 44 and at diametrically opposite sides of the posterior nose section portion 66 are diametrically opposed projections 78 in the form of ribs extending lengthwise of the jaws and nose section. These ribs are located in the jaw plane P1 and include posterior portions 78a on and extending virtually the full length of the jaws and shorter anterior portions 78b on the nose section 64. The anterior and posterior portions of each rib are joined at their radially outer sides by an integral thin flexible connecting portion 78c. The flexible connecting portions 78c (FIG. 4A) form the hinges 72 which pivotally connect the jaws 44 to the nose section 64. The finger pads 48 are mounted on the radially outer sides of the posterior rib portions 78a adjacent the posterior ends 42 of the jaws 44.

The insertion device and lens supporting means 56 on the tray 32 includes a nose section support sleeve 80 fixed to and extending forwardly from an upstanding wall 81 along the rear edge of the tray. The nose section sleeve is located midway between the side edges of the tray and has a central axis extending in the fore and aft direction of the tray parallel to upper surface of the tray. This sleeve axis is spaced above the upper tray surface a distance approximating the common external radius of the jaws 44 and the posterior nose section portion 66 of the lens insertion device 24. Nose section support sleeve 80 is internally and longitudinally sized to removably receive and support the anterior tip portion 68 of the insertion device nose section 64 in the manner shown best in FIG. 2. Extending coaxially through the nose section sleeve is a pin 82 which is sized to fit removably within the anterior end of the nose section passage 70, thus to maintain the shape of thin-walled nose section 68 during shipping and handling by means of sleeve 80 and pin 82.

Figure 15:
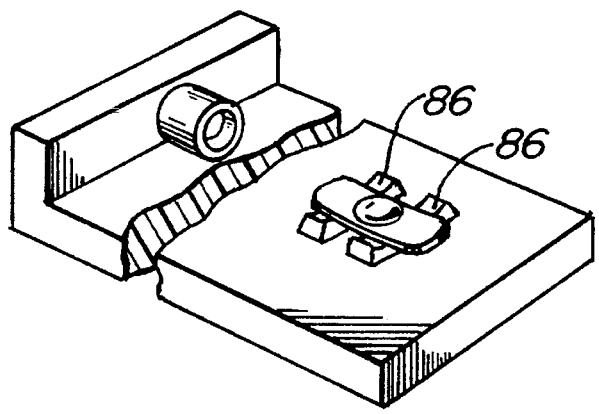
FIG. 15 is a reduced perspective view showing an intraocular lens supported on the instrument tray.

The insertion device and lens supporting means 56 on the tray 32 further comprises a cradle-like lens support 84 fixed to the tray in centered relation to a plane P2, hereafter referred to as a nose section sleeve plane, normal to the tray and containing the axis of the nose section support sleeve 80. This lens support has one or two pair of inclined ramps 86 (FIGS. 8, 10 and 15) which are located substantially equal distances to opposite sides of the nose section sleeve plane P2 and slope upwardly toward the latter plane. The high inner edges of the ramps are disposed in a common plane P3 normal to the nose section sleeve plane P2 and parallel to the upper surface of the tray 32. The common plane P3 is spaced above the upper tray surface a distance less than the outer radius of the jaws 44 of the insertion device 24. Between the high inner ends of the ramps is a concave recess 88 which is substantially bisected by the nose section sleeve plane P2.

The tray 32 and its supporting means 56 are constructed and arranged to receive the foldable intraocular lens 22 and the lens insertion device 24 in their storage positions of FIGS. 1, 2, 2A with the lens in its normal unfolded configuration and the jaws 44 of the insertion device in their normal wide open positions. In these storage positions, the unfolded lens rests on the upper inner edges of the lens support ramps 86 with the earlier mentioned longitudinal axis of the lens located substantially in the nose section sleeve plane P2. The anterior tip portion 68 of the insertion device is positioned within the nose section support sleeve 80, and the lower longitudinal edges of the open jaws 44 of the insertion device rest on the tray 32. The open jaws straddle the unfolded lens 22 and the lens support 84. Fixed to the tray 32 at one side of the lens support 84 is a lens hold-down device 90 in the form of a spring having arcuate spring arms 92. These spring arms extend laterally over and bear downwardly against the open jaws 44 and have intermediate downwardly bowed portions 94 which protrude downwardly between the open jaws 44 and press downwardly against the lens haptics 38. Joining the downwardly bowed spring arm portions 94 is a connecting spring portion 96 having an intermediate upwardly bowed portion which extends over and engages the lens optic 36. The hold-down spring 90 presses lightly against the unfolded lens 22 and the jaws 44 to hold the lens downwardly against the lens support 84 and the jaws against the tray 32. The pressure of the spring against the lens depresses the longitudinal center portion of the lens slightly into the shallow lens support recess 88 and thereby deflects the longitudinal edges of the lens upwardly slightly relative to the longitudinal center portion of the lens, as shown in FIG. 2A.

From the above description, it will be understood that in its storage position of FIGS. 1, 2, 2A on the tray 23, the unfolded lens 22 is positioned between the open jaws 44 of the insertion device 24 and substantially in the plane P3 (hereafter referred to as the lens storage plane) with the longitudinal edges of the lens inclined upwardly slightly relative to the latter plane. In this position, the lens is substantially bisected laterally by the nose section sleeve plane P2, and is disposed in a plane (i.e. the lens storage plane P3) which parallels the jaw plane P1 and intersects the concave inner sides 50 of the open jaws 44 between the jaw plane P1 and the lower jaw edges which rest on the tray 32. The lens then has longitudinal edge portions located at opposite sides of the nose section sleeve plane P2 and an intervening mid portion including the optic 36 between these edge portions.

The cover 34 of the handling or shipping case 30 is hinged to the upstanding base wail 81 and has a normal closed position, shown in broken lines in FIG. 2, in which the cover forms an enclosure for holding the lens 22 and lens insertion device 24 in their storage positions. The case, lens, and lens insertion device are sterilized in a package and maintained in a sterile condition until needed for a lens implantation. Mounted on the inside of the cover is a stop 100 which is located opposite the posterior ends 42 of the open jaws 44 of the lens insertion device 24 when the cover is closed. This stop holds the nose section of the insertion device in the nose section support sleeve 80 and thereby retains the insertion device in its storage position on the tray 32.

The illustrated instrument handle 26 includes a cylindrical tubular hand piece 102 whose anterior and posterior ends 58, 60 are open and whose posterior end is internally threaded. The hand piece 102 has a sidewall opening 104 including a posterior portion 106 which occupies approximately one half of the hand piece circumference and a pair of diametrically opposed slots 108 which extend forwardly along the hand piece from opposite circumferential ends of the posterior opening portion 106. The lens ejection means 62 of the handle 26 comprises a plunger including an elongate stem 110 having a posterior portion 112 threaded in the posterior end of the hand piece and a knurled knob 114 fixed on the posterior end of the stem. The stem 110 does not necessarily rotate when the knob 114 is turned, there being a rotating connection between these components.

The circular opening through the hand piece 26 is sized in diameter to slidably receive the lens insertion device 24 with its jaws 44 closed. The hand piece slots 108 are sized in width to slidably receive the ribs 78 on the lens insertion device. The posterior portion 106 of the sidewall opening 104 is sized circumferentially and longitudinally of the hand piece to permit assembly of the lens insertion device 24 in the hand piece 102 by lateral insertion of the insertion device through the posterior portion 106 of the side wall opening 104 followed by forward longitudinal movement of the insertion device through the hand piece, in the manner illustrated in FIG. 11. The plunger stem 110 has a length approximating the length of the tubular hand piece 102.

According to the preferred practice of the invention, the ophthalmic kit 20 and ophthalmic instrument 28 of the invention are used in the following way. The ophthalmic kit 20 and instrument handle 26 are provided in a sterile condition to the operating room in which the foldable lens 22 is to be implanted in a patient's eye. The kit is delivered to the operating room in its sealed sterile condition and is opened by surgical personnel in the operating room. The handle is sterilized and provided to the operating room separately from the kit. After opening the sterile kit 20 in the operating room, the jaws 44 of the lens insertion device 24 are squeezed closed by gripping the finger pads 48 between the thumb and forefinger while the insertion device remains on the tray 32, as illustrated in FIG. 7. During initial closure of the jaws, the unfolded lens is held down against the lens support 84 along the longitudinal centerline of the lens by the hold down spring 90, the longitudinal edges of the lens engage the concave inner sides of the jaws between the jaw plane P1 and the lower edges of the jaws, and the closing jaws ride upwardly along the ramps 86. This initial jaw closure occurs in such manner that the lens is initially compressed laterally edgewise between the jaws, and the longitudinal edge portions of the lens at opposite sides of the nose section sleeve plane P2 are folded upwardly, as shown in FIG. 8. During continued closure of the jaws to their fully closed positions of FIG. 9, the jaws cam the hold-down spring 90 upwardly out of contact with the lens, ride further upwardly along the ramps 86, and fold the lens laterally to its final fully folded configuration of FIG. 9, all while the lens insertion device and lens remain on the tray 32. At this point, the folded lens is confined within the lens insertion passage 76 of the lens insertion device 24.

The finger grip on the finger pads 48 of the lens insertion device 24 is maintained following the above closure of its jaws 44 and utilized to first remove the insertion device from the tray 32, in the manner illustrated in FIG. 10, with the jaws 44 of the device held closed and gripping the lens 22 in its folded configuration of FIG. 9 within the lens insertion passage 76, and then assemble the insertion device in the tubular hand piece 102. The hold-down spring 90 is deflected upwardly to its broken line position of FIG. 10 during removal of the insertion device from the tray and then springs back to its normal solid line position of FIG. 10.

Figure 11:
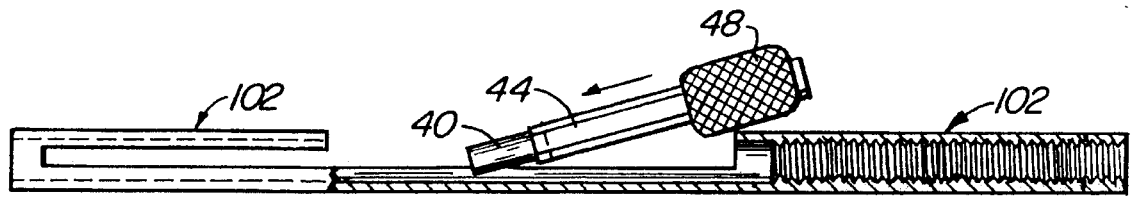
FIG. 11 illustrates the manner in which the handle and lens insertion device with the folded lens are assembled to form the ophthalmic instrument of the invention for inserting the folded lens into a patient's eye.
Figure 12:
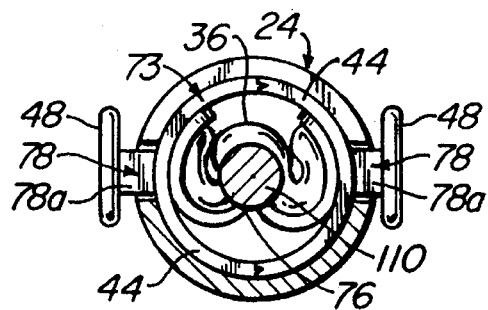
FIG. 12 is a transverse section through the fully assembled ophthalmic instrument.
Figure 13:
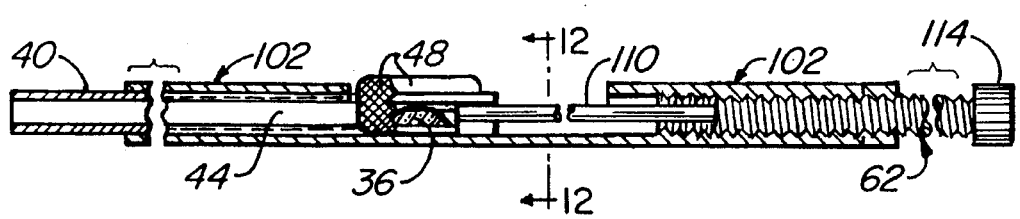
FIG. 13 is a longitudinal section through the fully assembled ophthalmic instrument illustrating the manner in which the folded lens is ejectable from the instrument by the handle plunger.

Assembly of the lens insertion device 24 in the hand piece 102 is accomplished by inserting the device through the posterior portion 106 of the side wall opening 104 in the hand piece lens and then sliding the device forwardly in the hand piece, in the manner illustrated in FIG. 11, all while gripping the finger pads 48 to hold the jaws 44 closed with the folded lens 22 gripped between the jaws. The lens ejection plunger 62 is retracted rearwardly in or removed from the hand piece during this assembly of the lens insertion device in the hand piece. The insertion device is moved forwardly in the hand piece to the fully assembled position of FIG. 13, wherein the anterior tip portion 68 of its nose section 64 projects beyond the anterior end 58 of the hand piece. In this fully assembled condition, the lens insertion device 24 and handle 26 form the ophthalmic lens insertion instrument 28, and the jaws 44 of the insertion device are held closed by the hand piece 102. The ribs 78 on the insertion device engage in the hand piece slots 108 and abut the anterior end walls of these slots to locate the insertion device relative to the hand piece about and along the axis of the hand piece. The finger pads 48 on the closed jaws 44 are located externally of the hand piece 102, as shown in FIG. 12.

Figure 14:
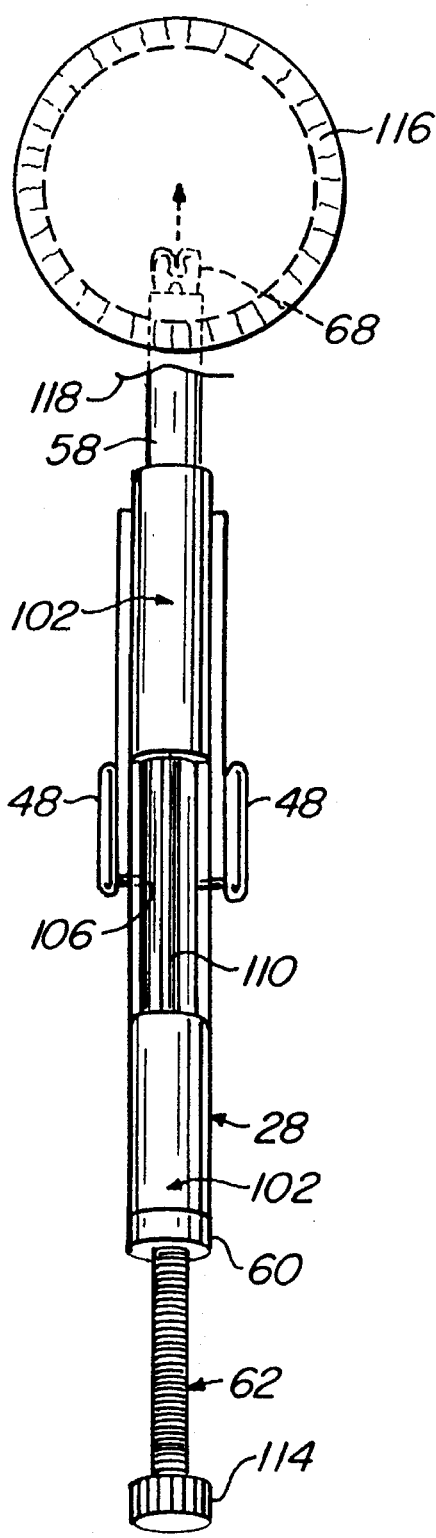
FIG. 14 illustrates the manner in which the ophthalmic instrument is used to implant the folded lens in a patient's eye.

The instrument 28 is now used in the manner illustrated in FIG. 14 to insert the folded lens 22 into the patient's eye 116 through a small incision 118 in the eye through which the natural lens had been previously removed from the eye. The lens 22 is inserted into the eye by first inserting the projecting anterior tip portion 68 of the instrument into the eye through the incision 118 and then rotating the knob 114 on the lens ejecting plunger 112 to move the plunger forwardly through the hand piece and the lens insertion passage 76 in the lens insertion device 24 to push the folded lens 22 through the passage into the eye. The folded lens stores elastic strain energy which unfolds the lens in the eye.

According to the preferred practice of the invention, the lens insertion device 24 is made to be disposable after one use. The handle 26 is made to be reusable. The entire lens implantation procedure occurs without physical contact of a person with the lens or contact of the lens with the external tissues of the eye, and these facts coupled with disposal of the lens insertion device after each use substantially eliminates the possibility of contamination of the lens.

I claim:

1. An ophthalmic kit for intraocular lens implantation, comprising:

a foldable intraocular lens having a normally unfolded configuration and foldable to a relatively compact folded configuration wherein the lens is conditioned for insertion into a patient's eye through a small corneal incision in the eye and the folded lens stores elastic strain energy for unfolding the lens within the eye, a lens insertion device having an anterior end insertable into the patient's eye through said incision and an opposite posterior end having a pair of lens gripping jaws having confronting inner concave sides and movable away from one another to open positions wherein the jaws are spaced to receive said lens in its unfolded configuration between said inner concave sides and toward one another to closed positions wherein said inner concave sides form a passage extending longitudinally through and opening through said anterior end of said device, and jaw closing means mounted directly on said jaws to be gripped between a user's fingers for squeezing said jaws together from their open positions to their closed positions, a handling case for holding said insertion device and lens until needed for lens implantation comprising a tray, and supporting means on the tray removably supporting said insertion device and said foldable lens in storage positions on the tray wherein (a) said jaws occupy their open positions, (b) said lens is positioned between the jaws with the lens in its normal unfolded configuration, and (c) said jaw closing means are located at one side of the tray to be gripped between the user's fingers for initially squeezing said jaws closed about the lens in a manner to fold the lens to its compact folded configuration within said passage while said insertion device and lens remain on the tray and thereafter removing the insertion device and folded lens from the tray, and wherein the folded lens is ejectable from the insertion device by passing it anteriorly from said passage through said anterior end of the device into a patient's eye following removal of said device from said tray.

2. An ophthalmic kit according to claim 1 wherein:

said jaw closing means comprise finger pads mounted on outer sides of said jaws which may be gripped between the fingers to close the jaws and then remove the insertion device and folded lens from said tray.

3. An ophthalmic kit according to claim 1 wherein:

said passage has a longitudinal axis, and said jaws are movable between their open and closed positions parallel to a jaw plane containing said longitudinal axis, and said supporting means includes lens supporting means supporting said lens in its unfolded configuration on said tray with the lens disposed in a lens plane of said tray and with one side of the lens facing normally upward away from the tray, and device supporting means supporting said insertion device on said tray in a position such that (a) said jaw plane and said lens plane are substantially parallel to one another, (b) said jaws have longitudinal edges adjacent said tray, (c) said lens plane intersects said concave jaw surfaces between said jaw plane and said jaw edges, and (d) a third plane transverse to said lens plane and said jaw plane and containing said longitudinal axis substantially bisects said lens, whereby the lens has laterally opposite edge portions at opposite sides of said third plane and an intervening mid portion between said laterally opposite edge portions.

4. An ophthalmic kit according to claim 1 including:

means connected to said insertion device for ejecting the folded lens from said insertion device through said anterior end of the device by moving the folded lens anteriorly through the device.

5. An ophthalmic kit according to claim 1 including:

a hand piece having anterior and posterior ends for removably receiving said insertion device and foldable lens in an assembled position wherein said hand piece holds said jaws closed with the lens gripped in its folded configuration between the jaws and the anterior end of said insertion device projects beyond the anterior end of the hand piece for insertion into the patient's eye, and lens ejection means on said hand piece for ejecting the folded lens from said insertion device through said anterior end of said insertion device.

6. An ophthalmic kit according to claim 1 including:

a tubular hand piece having an open anterior end and a posterior end for removably receiving said insertion device and foldable lens in an assembled position within said hand piece wherein (a) said insertion device extends longitudinally through said hand piece with the anterior end of said insertion device projecting beyond the anterior end of the hand piece for insertion into the patient's eye, and (b) said hand piece holds said jaws closed with the lens gripped in its folded configuration between the jaws, and lens ejector means on said hand piece for ejecting the folded lens from said insertion device through said anterior end of said insertion device.

7. An ophthalmic kit according to claim 1 including:

a tubular hand piece having an open anterior end and a posterior end for removably receiving said insertion device and foldable lens in an assembled position within said hand piece wherein (a) said insertion device extends longitudinally through said hand piece with the anterior end of said insertion device projecting beyond the anterior end of the hand piece for insertion into the patient's eye, and (b) said hand piece holds said jaws closed with the lens gripped in its folded configuration between the jaws, and a lens ejection plunger entering said posterior end of said hand piece and movable forwardly through the hand piece for ejecting the folded lens from said insertion device through said anterior end of said insertion device.

8. An ophthalmic kit according to claim 1 wherein:

said handling case includes a cover forming with the tray an enclosure for containing said insertion device and foldable lens in a sterile condition until needed for lens implantation, and said cover is adapted to be opened to permit removal of said insertion device and lens from the tray.

9. An ophthalmic kit for intraocular lens implantation, comprising:

a foldable intraocular lens having a normally unfolded configuration and foldable to a relatively compact folded configuration wherein the lens is conditioned for insertion into a patient's eye through a small corneal incision in the eye and the folded lens stores elastic strain energy for unfolding the lens within the eye, a lens insertion device having a normally anterior end insertable into the patient's eye through said incision and an opposite posterior end and including a pair of lens gripping jaws movable away from one another to positions and toward one another to closed positions, and jaw closing means mounted directly on said insertion device for moving said jaws from their open positions to their closed positions, a handling case for holding said insertion device and lens until needed for lens implantation comprising a tray, and supporting means on the tray removably supporting said insertion device and said foldable lens in storage positions on the tray wherein (a) said jaws occupy their open positions, (b) said lens is positioned between the jaws with the lens in its normally unfolded configuration, and (c) said jaw closing means are accessible for closing said jaws about the lens in a manner to fold the lens to its compact folded configuration while said insertion device and lens remain on the tray, and wherein said insertion device and lens are removable from said tray with said jaws closed and gripping said lens in its folded configuration, yieldable lens hold-down means on said tray over said lens supporting means which yieldably engage said lens between said laterally opposite lens portions to yieldably hold the lens downwardly against said lens supporting means and which hold-down means is retracted upwardly from the lens during closure of said jaws, whereby closure of said jaws folds said laterally opposite lens portions upwardly away from said tray relative to said lens mid portion during closure of said jaws, means on said tray for moving said jaws upwardly away from said tray relative to said lens supporting means during closure of the jaws to aid upward folding of said laterally opposite lens portions relative to said lens mid portion during closure of the jaws, the folded lens is ejectable from the insertion device through said anterior end of the device into a patient's eye following insertion of said anterior end of the device into the eye, said jaws have confronting concave inner surfaces and opposite outer sides, and said inner concave surfaces are generally cylindrically curved about axes extending lengthwise of the respective jaws and form a passage coaxial with a longitudinal axis of the insertion device and opening through said anterior and posterior ends of said insertion device when said jaws are closed, said jaws are movable between their open and closed positions parallel to a jaw plane containing said longitudinal axis, and said supporting means includes lens supporting means supporting said lens in its unfolded configuration on said tray with the lens disposed in a lens plane of said tray and with one side of the lens facing normally upward away from the tray, and means supporting said insertion device on said tray in a position such that (a) said jaw plane and lens plane substantially parallel one another, (b) said jaws have longitudinal edges adjacent said tray, (c) said lens plane intersects said concave jaw surfaces between said jaw plane and said jaw edges, and (d) a third plane transverse to said lens plane and jaw plane and containing said longitudinal axis substantially bisects said lens, whereby the lens has laterally opposite edge portions at opposite sides of said third plane and an intervening mid portion between said laterally opposite edge portions.

10. An ophthalmic kit for intraocular lens implantation, comprising:

a foldable intraocular lens having a normally unfolded configuration and foldable to a relatively compact folded configuration wherein the lens is conditioned for insertion into a patient's eye through a small corneal incision in the eye and the folded lens stores elastic strain energy for unfolding the lens within the eye, a lens insertion device having an anterior end insertable into the patient's eye through said incision and an opposite posterior end and including a pair of lens gripping jaws movable away from one another to open positions and toward one another to closed positions, and jaw closing means mounted directly on said insertion device for moving said jaws from their open positions to their closed positions, a handling case for holding said insertion device and lens until needed for lens implantation comprising a tray and supporting means on the tray removably supporting said insertion device and said foldable lens in storage positions on the tray wherein (a) said jaws occupy their open positions, (b) said lens is positioned between the jaws with the lens in its normal unfolded configuration, and c) said jaw closing means are accessible for closing said jaws about the lens in a manner to fold the lens to its compact folded configuration while said insertion device and lens remain on the tray, a tubular hand piece having an open anterior end and a posterior end for removably receiving said insertion device and foldable lens in an assembled position within said hand piece wherein (a) said insertion device extends longitudinally through said hand piece with the anterior end of said insertion device projecting beyond the anterior end of the hand piece for insertion into the patient's eye, and (b) said hand piece holds said jaws closed with the lens gripped in its folded configuration between the jaws, a lens ejection plunger entering the posterior end of said hand piece and movable forwardly through the hand piece for ejecting the folded lens from said insertion device through said anterior end of said insertion device, and wherein said insertion device and lens are removable from said tray with said jaws closed and gripping said lens in its folded configuration, the folded lens is ejectable from the insertion device through said anterior end of the device into a patient's eye following insertion of said anterior end of the device into the eye, said insertion device has a longitudinal axis, and said jaws are movable between open and closed positions parallel to a jaw plane containing said axis, said hand piece has a side wall opening including a posterior portion through which said insertion device is insertable into said hand piece and a pair of diametrically opposed longitudinal side wall slots extending forwardly from said posterior portion of said side wall opening and having anterior end walls, said jaws have confronting inner sides, opposite outer sides, and radial projections along said outer sides which are located in a common jaw plane containing said longitudinal axis, said insertion device is insertable into said hand piece through said posterior portion of said side wall opening and is then movable forwardly in the hand piece in such a way that said jaw projections enter said hand piece slots and engage said slot end walls to position said insertion device longitudinally and rotationally in the hand piece when said injection device occupies said assembled position within the hand piece, and said jaw closing means comprise finger pads which are secured to the outer sides of said jaws and project externally of said hand piece through said side wall opening when said insertion device occupies said assembled position in the hand piece.

11. An ophthalmic kit according to claim 10 wherein:

said confronting inner sides of said jaws are concave and form a passage coaxial with said longitudinal axis of said insertion device and opening through said anterior and posterior ends of said insertion device when said jaws are closed, said foldable lens when gripped in its folded configuration between said jaws is positioned within said passage, and said plunger and the posterior end of said hand piece have mating threads for effecting anterior movement of the plunger through said passage to push the folded lens anteriorly through said passage into the patient's eye by rotation of said plunger relative to said hand piece after insertion of said anterior end of the insertion device into the eye.

12. An ophthalmic kit according to claim 10 wherein:

said jaws have concave inner surfaces at said inner sides of the jaws which are generally cylindrically curved about axes extending lengthwise of the respective jaws and form a passage coaxial with said longitudinal axis of said insertion device and opening through said anterior and posterior ends of said insertion device when said jaws are closed, said jaws are movable between their open and closed positions parallel to a jaw plane containing said longitudinal axis, and said supporting means includes lens supporting means supporting said lens in its unfolded configuration on said tray with the lens disposed in a lens plane of said tray and with one side of the lens facing normally upward away from the tray, and means supporting said insertion device on said tray in a position such that (a) said jaw plane and said lens plane substantially parallel one another, (b) said jaws have longitudinal edges adjacent said tray, (c) said lens plane intersects said concave jaw surfaces between said jaw plane and said jaw edges, and (d) a third plane transverse to said lens plane and jaw plane and containing said longitudinal axis substantially bisects said lens, whereby the lens has laterally opposite portions located at opposite sides of said third plane and an intervening mid portion between said laterally opposite portions.

13. An ophthalmic kit according to claim 12 including:

yieldable lens hold-down means on said tray over said lens supporting means which yieldably engage said lens between said laterally opposite lens portions to yieldably hold the lens downwardly against said lens supporting means and which hold-down means is retracted upwardly from the lens during closure of said jaws, whereby closure of said jaws folds said laterally opposite lens portions upwardly away from said tray relative to said lens mid portion during closure of said jaws, and means on said tray for moving said jaws upwardly away from said tray relative to said lens supporting means during closure of the jaws to aid upward folding of said laterally opposite lens portions relative to said lens mid portion during closure of the jaws.

14. An ophthalmic kit according to claim 10 wherein:

said jaws have confronting inner longitudinal edges with mating tongue and groove formations which interengage when the jaws are closed to coaxially align the jaws relative to each other.

15. An ophthalmic kit for intraocular lens implantation, comprising:

a foldable intraocular lens having a normally unfolded configuration and foldable to a relatively compact folded configuration wherein the lens is conditioned for insertion into a patient's eye through a small incision in the eye and the lens stores elastic strain energy for unfolding the lens within the eye, a lens insertion device including (a) a tubular anterior nose section having a relatively slender anterior tip portion for insertion into the patient's eye, a posterior end, and a nose section passage extending longitudinally through said nose section, (b) lens gripping jaws extending rearwardly from the posterior end of said nose section and having anterior ends secured to the posterior end of said nose section at opposite sides of said passage and posterior free ends movable toward one another to closed positions and away from one another to open positions, and (c) jaw closing means connected to said jaws and engagable by a user for closing said jaws, a handling case for holding said insertion device and lens until needed for lens implantation including a tray, and means on the tray removably supporting said insertion device and said foldable lens in storage positions on the tray wherein (a) said jaws occupy their open positions, (b) said foldable lens is positioned between the free ends of said jaws with the lens in its normal unfolded configuration, and (c) said jaw closing means are accessible for closing said jaws about the lens in a manner to fold the lens to its compact folded configuration while said insertion device and lens are on the tray, and wherein said insertion device and lens are removable from said tray with said jaws closed about and gripping said lens in its folded configuration, and said passage opens posteriorly between said jaws, whereby the folded lens can be inserted into the patient's eye by inserting said anterior tip portion into the eye and then ejecting the folded lens anteriorly between the jaws and through said passage into the eye.

16. An ophthalmic kit according to claim 15 wherein:

said jaws have confronting inner sides and opposite outer sides, and said jaw closing means comprise finger pads mounted on the outer sides of said jaws which may be gripped between the fingers to close the jaws and then remove the insertion device and folded lens from said tray.

17. An ophthalmic kit according to claim 15 wherein:

said jaws have confronting inner concave sides which form a jaw passage coaxial with and opening anteriorly to said nose section passage when said jaws are closed, said nose section passage and said jaw passage form a lens insertion passage extending through said lens insertion device, and said lens when gripped in its folded configuration between said jaws is positioned within said lens insertion passage and is ejectable anteriorly through said lens insertion passage into the patient's eye after insertion of said anterior tip portion of said lens insertion device into the patient's eye.

18. An ophthalmic kit according to claim 15 wherein:

said jaws have confronting inner sides and opposite outer sides, said jaw closing means comprise finger pads fixed to the outer sides of said jaws which may be gripped between the fingers to close the jaws and then remove the insertion device and folded lens from said tray, said inner confronting sides of said jaws are concave and form a jaw passage coaxial with and opening anteriorly to said nose section passage when said jaws are closed, said nose section passage and said jaw passage form a lens insertion passage extending through said lens insertion device, and said foldable lens when gripped in its folded configuration between said jaws is positioned within said lens insertion passage and is ejectable anteriorly through said lens insertion passage into the patient's eye after insertion of said anterior tip portion of said insertion device into the eye.

19. An ophthalmic kit according to claim 18 wherein:

said jaws have confronting inner longitudinal edges with mating tongue and groove formations which interengage when the jaws are closed to coaxially align the jaws relative to each other and to position the jaw passage coaxial with said nose section passage.

20. An ophthalmic kit according to claim 17, and further including:

pin means on said handling case for extending into said nose section passage to maintain the configuration thereof during shipping and handling.

21. An ophthalmic kit according to claim 20, and further including:

a support sleeve coaxial with the pin means for cooperating with the pin means to receive the nose section passage therebetween.

22. An ophthalmic kit according to claim 15 wherein:

said jaws have confronting inner longitudinal edges with mating tongue and groove formations which interengage when the jaws are closed to coaxially align the jaws relative to each other.

23. An ophthalmic kit according to claim 15 wherein:

said jaws have confronting concave inner surfaces and opposite outer sides, and said inner concave surfaces are generally cylindrically curved about axes extending lengthwise of the respective jaws and forming a jaw passage coaxially aligned with and opening anteriorly to said nose section passage when said jaws are closed, said nose section passage and said jaw passage form a lens insertion passage extending through said lens insertion device and having a longitudinal axis, said jaws are movable between their open and closed positions parallel to a jaw plane containing said longitudinal axis, said supporting means includes lens supporting means supporting said lens in its unfolded configuration on said tray with the lens disposed in a lens plane of said tray and with one side of the lens facing normally upward away from the tray, and means supporting said insertion device on said tray in a position such that (a) said jaw plane and said lens plane substantially parallel one another, (b) said jaws have longitudinal edges adjacent said tray, (c) said lens plane intersects said concave jaw surfaces between said jaw plane and jaw edges, and (d) a third plane transverse to said lens plane and jaw plane and containing said longitudinal axis substantially bisects said lens, whereby the lens has laterally opposite portions located at opposite sides of said third plane and an intervening mid portion between said laterally opposite portions.

24. An ophthalmic kit according to claim 23 including:

yieldable lens hold-down means on said tray over said lens supporting means which yieldably engages said lens between said laterally opposite lens portions to yieldably hold the lens downwardly against said lens supporting means and which hold-down means is retracted upwardly from the lens during closure of said jaws, whereby closure of said jaws folds said laterally opposite lens portions upwardly away from said tray relative to said lens mid portion, and means on said tray for moving said jaws upwardly away from said tray relative to said lens supporting means during closure of the jaws to aid upward folding of said laterally opposite lens portions relative to said lens mid portion during closure of the jaws.

25. An ophthalmic kit according to claim 15 including:

a hand piece having anterior and posterior ends for removably receiving said insertion device and foldable lens in assembled position wherein said hand piece holds said jaws closed with the lens gripped in its folded configuration between the jaws and the anterior tip portion of said insertion device projects beyond the anterior end of the hand piece for insertion into the patient's eye, and lens ejection means on said hand piece for ejecting the folded lens from said insertion device through said anterior tip portion.

26. An ophthalmic kit according to claim 16 including:

a tubular hand piece having an open anterior end and a posterior end for removably receiving said insertion device and foldable lens in an assembled position within said hand piece wherein (a) said insertion device extends longitudinally through said hand piece with said anterior tip portion of the insertion device projecting beyond the anterior end of the hand piece for insertion into the patient's eye, and (b) said hand piece holds said jaws closed with the lens gripped in its folded configuration between the jaws, and lens ejecting means on said hand piece for ejecting the folded lens from said insertion device through said anterior end of said insertion device.

27. An ophthalmic kit according to claim 15 including:

a tubular hand piece having an open normally anterior end and a posterior end for removably receiving said insertion device and foldable lens in an assembled position within said hand piece wherein (a) said insertion device extends longitudinally through said hand piece with the anterior tip portion of said insertion device projecting beyond the anterior end of the hand piece for insertion into the patient's eye, and (b) said hand piece holds said jaws closed with the lens gripped in its folded configuration between the jaws, and a lens ejection plunger entering said posterior end of said hand piece and movable anteriorly through the hand piece for ejecting the folded lens from said insertion device through said anterior tip portion of said insertion device.

28. An ophthalmic kit according to claim 15 including:

a tubular hand piece having an open normally anterior end and a posterior end for removably receiving said insertion device and foldable lens in an assembled position within said hand piece wherein (a) said insertion device extends longitudinally through said hand piece with the anterior tip portion of said insertion device projecting beyond the anterior end of the hand piece for insertion into the patient's eye, and (b) said hand piece holds said jaws closed with the lens gripped in its folded configuration between the jaws, a lens ejection plunger entering the posterior end of said hand piece and movable anteriorly forwardly through the hand piece for ejecting the folded lens from said insertion device through said anterior tip portion of said insertion device, and wherein said hand piece has a side wall opening including a posterior portion through which said insertion device is insertable into said hand piece and a pair of diametrically opposed longitudinal side wall slots extending anteriorly from said posterior portion and having anterior end walls, said lens insertion device has a longitudinal axis, and said jaws are movable between open and closed positions parallel to a jaw plane containing said longitudinal axis, said jaws have confronting inner sides, opposite outer sides, and radial projections along said outer sides which are located in said jaw plane, said insertion device is insertable into said hand piece through said posterior portion of said side wall opening and is then movable anteriorly in the hand piece in such a way that said radial projections enter said hand piece slots and engage said slot end walls to position said insertion device longitudinally and rotationally in the hand piece when said injection device occupies said assembled position within the hand piece, and said jaw closing means comprise finger pads which are secured to the outer sides of said jaws and project externally of said hand piece through said side wall opening when said insertion device occupies said assembled position in the hand piece.

29. An ophthalmic kit according to claim 28 wherein:

the anterior ends of said jaws are pivotally hinged to the posterior end of said nose section at opposite sides of said nose section passage, said confronting inner sides of said jaws are concave and form a jaw passage coaxial with and opening forwardly to said nose section passage when said jaws are closed, said nose section passage and said jaw passage form a lens insertion passage extending through said lens insertion device, said foldable lens when gripped in its folded configuration between said jaws is positioned within said lens insertion passage, and said plunger and the posterior end of said hand piece have mating threads for effecting forward movement of the plunger through said lens insertion passage to push the folded lens anteriorly through said lens insertion passage into the patient's eye.

30. An ophthalmic kit according to claim 29, and further including:

pin means on said handling case for extending into said nose section passage to maintain the configuration thereof during shipping and handling.

31. An ophthalmic kit according to claim 30, and further including:

a support sleeve coaxial with the pin means for cooperating with the pin means to receive the nose section passage therebetween.

32. An ophthalmic kit according to claim 28 wherein:

said jaws have concave inner surfaces at said inner sides of the jaws which are generally cylindrically curved about axes extending lengthwise of the respective jaws and form a jaw passage coaxial and opening anteriorly to said insertion passage when said jaws are closed, said nose section passage and said jaw passage form a lens insertion passage having a longitudinal axis and extending through said lens insertion device, said jaws are movable between their open and closed positions parallel to a jaw plane containing said longitudinal axis, said supporting means includes lens supporting means supporting said lens in its unfolded configuration on said tray with the lens disposed in a lens plane of said tray and with one side of the lens facing normally upward away from the tray, and means supporting said insertion device on said tray in a position such that (a) said jaw plane and said lens plane substantially parallel one another, (b) said jaws have longitudinal edges adjacent said tray, (c) said lens plane intersects said concave jaw surfaces between said jaw plane and said jaw edges, and (d) a third plane transverse to said lens and jaw planes and containing said longitudinal axis substantially bisects said lens, whereby the lens has laterally opposite portions located at opposite sides of said third plane and an intervening mid portion between said laterally opposite portions, and said handling case includes lens yieldable hold-down means on said tray over said lens supporting means which yieldably engages said lens between said laterally opposite lens portions to yieldably hold the lens downwardly against said lens supporting means and which hold-down means is retracted upwardly from the lens during closure of said jaws, whereby closure of said jaws folds said laterally opposite lens portions upwardly away from said tray relative to said lens mid portion.

33. An ophthalmic kit according to claim 32 including:

means on said tray for moving said jaws upwardly away from said tray relative to said lens supporting means during closure of the jaws to aid upward folding of said laterally opposite lens portions relative to said lens mid portion during closure of the jaws.

34. An ophthalmic kit according to claim 15 wherein:

said handling case includes a cover forming with the tray an enclosure for containing said insertion device and foldable lens in a sterile condition until needed for lens implantation, and said cover is adapted to be opened to permit removal of said insertion device and lens from the tray.

35. An ophthalmic kit according to claim 15, and further including:

pin means on said handling case for extending into said nose section passage to maintain the configuration thereof during shipping and handling.

36. An ophthalmic kit according to claim 35, and further including:

a support sleeve coaxial with the pin means for cooperating with the pin means to receive the nose section passage therebetween.

37. An ophthalmic instrument for implanting a foldable intraocular lens in a patient's eye, comprising:

a lens insertion device having an anterior end insertable into the patient's eye and an opposite posterior end and including a tubular portion at one of said ends having a longitudinal axis and a passage extending axially through said tubular portion, a pair of lens gripping jaws extending generally lengthwise of said tubular portion from one end of said tubular portion and having ends adjacent said one end of said tubular portion and opposite ends remote from said one end of said tubular portion, means supporting said adjacent jaw ends on said one end of said tubular portion at opposite sides, respectively, of said passage in said tubular portion for movement of said opposite jaw ends parallel to a jaw plane containing said axis and away from one another to open positions and toward one another to closed positions, and jaw closing means connected to said jaws for moving said jaws from their open positions to their closed positions, and wherein said jaws have confronting inner sides, opposite outer sides, longitudinal edges which abut one another when said laws occupy their closed positions, and inner concave surfaces between their respective jaw edges which form a jaw passage coaxial with and opening endwise to said passage in said tubular portion to form a continuous lens insertion passage through and opening through said anterior end of said lens insertion device when said jaws occupy their closed positions, and said jaw closing means comprises finger pads permanently secured to the outer sides of said jaws and adapted to be gripped between the user's fingers for squeezing said jaws closed and then holding said insertion device whereby an intraocular lens can be inserted into an eye by folding it with the jaws and ejecting it anteriorly through the tubular portion.

38. An ophthalmic instrument according to claim 37 wherein:

said jaws are adapted to straddle a foldable intraocular lens when the jaws occupy their open positions and to be closed about the lens to fold the lens to and grip the lens in a relatively compact folded configuration, and said instrument includes lens ejection means connected to said lens insertion device for ejecting the folded lens from said instrument into the patient's eye by moving the folded lens anteriorly through said lens insertion passage.

39. An ophthalmic instrument according to claim 37 including:

a tubular hand piece having an open anterior end and a posterior end for removably receiving said insertion device in an assembled position within said hand piece wherein (a) said insertion device extends longitudinally through said hand piece with the anterior end of said insertion device projecting beyond the anterior end of the hand piece for insertion into the patient's eye, and (b) said hand piece holds said jaws closed, and wherein said jaws are adapted to straddle a foldable intraocular lens when the jaws occupy their open positions and to be closed about the lens to fold the lens to and grip the lens in a relatively compact folded configuration, and said hand piece includes lens ejection means for ejecting the folded lens from said insertion device by moving the folded lens anteriorly through said passage.

40. An ophthalmic instrument according to claim 37 including:

a tubular hand piece having an open anterior end and a posterior end for removably receiving said insertion device in an assembled position within said hand piece wherein (a) said insertion device extends longitudinally through said hand piece with the anterior end of said insertion device projecting beyond the anterior end of the hand piece for insertion into the patient's eye, and (b) said hand piece holds said jaws closed, and a lens ejection plunger entering said posterior end of said hand piece and movable longitudinally through the hand piece and said passage in said insertion device.

41. An ophthalmic instrument according to claim 40 wherein: said plunger is threaded in said hand piece.

42. An ophthalmic instrument for implanting a foldable intraocular lens in a patient's eye, comprising:

a lens insertion device having an anterior end insertable into the patient's eye and an opposite posterior end and including a pair of lens gripping jaws extending lengthwise of said insertion device and having anterior ends adjacent said anterior end of said insertion device and posterior ends adjacent said posterior end of said insertion device, means supporting said jaws at corresponding ends of the jaws for movement of the other ends of the jaws away from one another to open positions and toward one another to closed positions, and jaw closing means connected to said jaws for moving said jaws from their open positions to their closed positions, said jaws have confronting inner concave sides which form a passage opening through said anterior and posterior ends of said insertion device when said jaws occupy their closed positions, and opposite outer sides, a tubular hand piece having an open anterior end and a posterior end for removably receiving said insertion device in an assembled position within said hand piece wherein (a) said insertion device extends longitudinally through said hand piece with the anterior end of said insertion device projecting beyond the anterior end of the hand piece for insertion into the patient's eye, and (b) said hand piece holds said jaws closed, a lens ejection plunger entering the posterior end of said hand piece and movable longitudinally through the hand piece and said passage, and wherein said insertion device has a longitudinal axis, and said jaws are movable between open and closed positions parallel to a plane containing said axis, said jaws have radial projections along said outer sides located in said plane, said hand piece has a side wall opening including a posterior portion through which said insertion device is insertable into said hand piece and a pair of diametrically opposed longitudinal side wall slots extending anteriorly from said posterior portion of said side wall opening and having anterior end walls, said insertion device is insertable into said hand piece through said posterior portion of said side wall opening and is then movable anteriorly in the hand piece in such a way that in said assembled position, said jaw projections enter said hand piece slots and engage said slot end walls to position said insertion device longitudinally and rotationally in the hand piece, and said jaw closing means comprise finger pads which are secured to the outer sides of said jaws and project externally of said hand piece through said side wall opening when said insertion device occupies said assembled position in the hand piece.

43. An ophthalmic instrument for implanting a foldable intraocular lens in a patient's eye, comprising:

a lens insertion device including (a) a tubular nose section having a relatively slender anterior tip portion for insertion into the patient's eye, a posterior end, and a nose section passage having a longitudinal axis and extending longitudinally through said nose section and opening anteriorly through said anterior tip portion and posteriorly through said posterior end of said nose section, (b) lens gripping jaws extending posteriorly from the posterior end of said nose section at opposite sides of said axis and in a common plane containing said axis and having anterior ends secured to the posterior end of said nose section at opposite sides, respectively, of said nose section passage and posterior free ends movable toward one another parallel to said plane to closed positions and away from one another parallel to said plane to open positions, and (c) jaw closing means on said jaws for receiving opposing forces for closing said jaws whereby an intraocular lens can be inserted into an eye by folding it with the jaws and ejecting it anteriorly through the passage of the nose section.

44. An ophthalmic instrument according to claim 43 wherein:

said jaws have confronting inner sides and opposite outer sides, and said jaw closing means comprise finger pads mounted on the outer sides of said jaws which may be gripped between the fingers to close the jaws and then hold the insertion device.

45. An ophthalmic instrument according to claim 43 wherein:

said jaws have confronting inner concave sides which form a jaw passage coaxial with and opening anteriorly to said nose section passage and rearwardly at the posterior ends of said jaws when said jaws are closed, and said nose section passage and said jaw passage form a lens insertion passage extending longitudinally through said insertion device.

46. An ophthalmic instrument according to claim 43 wherein:

said jaws have confronting inner concave sides which form a jaw passage coaxial with and opening anteriorly to said nose section passage and posteriorly at the posterior ends of said jaws when said jaws are closed, said nose section passage and said jaw passage form a lens insertion passage extending longitudinally through said insertion device, said jaws are adapted to straddle a foldable intraocular lens when the jaws occupy their open positions and to be closed about the lens to fold the lens to and grip the lens in a relatively compact folded configuration, and said instrument includes lens ejection means connected to said lens insertion device for ejecting the folded lens from said instrument into the patient's eye by moving the folded lens anteriorly through said lens insertion passage.

47. An ophthalmic instrument according to claim 43 including:

a hand piece having anterior and posterior ends and removably receiving said insertion device in an assembled position wherein said hand piece holds said jaws closed, and said anterior tip portion of said insertion device projects beyond the anterior end of the hand piece for insertion into the patient's eye, and wherein said jaws have confronting inner concave sides which form a law passage coaxial with and opening anteriorly to said nose section passage and posteriorly at the posterior ends of said jaws when said jaws are closed, said nose section passage and said jaw passage form a lens insertion passage extending longitudinally through said insertion device, said jaws are adapted to straddle a foldable intraocular lens when the jaws occupy their open positions and to be closed about the lens to fold the lens to and grip the lens in a relatively compact folded configuration, and said instrument includes lens ejection means on said handpiece for ejecting the folded lens from said insertion device by moving the folded lens anteriorly through said lens insertion passage.

48. An ophthalmic instrument according to claim 43 including:

a tubular hand piece having an open anterior end and a posterior end for removably receiving said insertion device in an assembled position within said hand piece wherein (a) said insertion device extends longitudinally through said hand piece with the anterior tip portion of said insertion device projecting beyond the anterior end of the hand piece for insertion into the patient's eye, and (b) said hand piece holds said jaws closed, and wherein said jaws have confronting inner concave sides which form a jaw passage coaxial with and opening anteriorly to said nose section passage and posteriorly at the posterior ends of said jaws when said jaws are closed, said nose section passage and said jaw passage form a lens insertion passage extending longitudinally through said insertion device, said jaws are adapted to straddle a foldable intraocular lens when the jaws occupy their open positions and to be closed about the lens to fold the lens to and grip the lens in a relatively compact folded configuration, and said handpiece includes lens ejection means movable through said nose section passage for ejecting the folded lens from said insertion device by moving the folded lens, anteriorly through said lens insertion passage.

49. An ophthalmic instrument according to claim 43 including:

a tubular hand piece having an open anterior end and a posterior end and removably receiving said insertion device in an assembled position within said hand piece wherein (a) said insertion device extends longitudinally through said hand piece with the anterior end of said insertion device projecting beyond the anterior end of the hand piece for insertion into the patient's eye, and (b) said hand piece holds said jaws closed, and a lens ejection plunger entering said posterior end of said hand piece and movable longitudinally through the hand piece and passage.

50. An ophthalmic instrument for implanting a foldable intraocular lens in a patient's eye, comprising:

a lens insertion device including (a) a tubular nose section having a relatively slender anterior tip portion for insertion into the patient's eye and a posterior end, and a nose section passage having a longitudinal axis and extending longitudinally through said nose section and opening anteriorly through said anterior tip portion and posteriorly through said posterior end of said nose section, (b) lens gripping jaws extending posteriorly from the posterior end of said nose section at opposite sides of said axis and having anterior ends secured to the posterior end of said nose section at opposite sides, respectively, of said nose section passage and posterior free ends movable toward one another in a plane containing said axis to closed positions and away from one another in said plane to open positions, and (c) jaw closing means connected to said jaws for engagement by a user to close said jaws, a tubular hand piece having an open anterior end and a posterior end and removably receiving said insertion device and foldable lens in an assembled position within said hand piece wherein (a) said insertion device extends longitudinally through said hand piece with the anterior tip portion of said insertion device projecting beyond the anterior end of the hand piece for insertion into the patient's eye, and (b) said hand piece holds said jaws closed, a lens ejection plunger entering the posterior end of said hand piece and movable longitudinally through the hand piece and said passage, and wherein said insertion device has a longitudinal axis, and said jaws are movable between open and closed positions parallel to a plane containing said axis, said jaws have confronting inner sides, opposite outer sides, and radial projections along said outer sides which are located in said plane, said hand piece has a side wall opening including a posterior portion through which said insertion device is insertable into said hand piece and a pair of diametrically opposed longitudinal side wall slots extending anteriorly from said posterior portion of said side wall opening and having anterior end walls, and said insertion device is insertable into said hand piece through said posterior portion of said side wall opening and is then movable anteriorly in the hand piece in such a way that in said assembled position, said jaw projections enter said hand piece slots and engage said slot end walls to position said insertion device longitudinally and rotationally in the hand piece, and said jaw closing means comprise finger pads which are secured to the outer sides of said jaws and project externally of said hand piece through said side wall opening when said insertion device occupies said assembled position in the hand piece.

51. A handle for an ophthalmic instrument for implanting a foldable intraocular lens into a patient's eye, comprising:

a tubular hand piece comprising a tube having open anterior and posterior ends and a sidewall containing a sidewall opening between said ends including (a) a posterior portion extending circumferentially about at least one half the tube circumference and having opposite ends spaced circumferentially of the tube, and (b) a pair of diametrically opposed longitudinal slots extending anteriorly along the tube from said ends of said posterior portion and having anterior end walls.

52. A handle according to claim 51 including:

a plunger entering the posterior end of said hand piece and movable longitudinally through the hand piece.

53. An ophthalmic method of inserting into a patient's eye through a corneal incision in the eye a foldable intraocular lens which has a normal unfolded configuration and is foldable into a compact folded configuration wherein the lens stores elastic strain energy for unfolding the lens, said method comprises the steps of:

providing a lens insertion instrument including (a) a lens insertion device having a slender anterior tip portion for insertion into a patient's eye through a corneal incision in the eye, a posterior end, and lens gripping jaws which are movable between open positions and closed positions and have confronting concave inner sides which form a passage opening through said tip portion and said posterior end of said device when the jaws are closed, (b) a hand piece having anterior and posterior ends for receiving said insertion device in an assembled position in the hand piece wherein said anterior tip portion of the device projects beyond the anterior end of the hand piece, and (c) a plunger movable longitudinally through the hand piece and said passage when said insertion device occupies said assembled position in the hand piece, storing said lens in its unfolded configuration and said insertion device on a tray with said jaws of the device straddling the unfolded lens, closing said jaws about said lens to fold the lens to its folded configuration and confine the lens in said passage just prior to insertion of the lens into a patient's eye and while said insertion device and lens are on said tray, removing said insertion device from said tray and placing the device in said assembled position in said hand piece all while said jaws remain closed and confine the folded lens in said passage, inserting said tip portion of said insertion device into the patient's eye through said corneal incision, and moving said plunger anteriorly through said passage to push the folded lens forwardly through said passage in the tip portion and into the parent's eye.

54. An ophthalmic kit for intraocular lens implantation, comprising:

a foldable intraocular lens having a normally unfolded configuration and foldable to a relatively compact folded configuration wherein the lens is conditioned for insertion into a patient's eye through a small corneal incision in the eye and the folded lens stores elastic strain energy for unfolding the lens within the eye, a lens insertion device having an anterior end insertable into the patient's eye through said incision and an opposite posterior end and including a pair of lens gripping jaws movable away from one another to open positions and toward one another to closed positions, and jaw closing means mounted directly on said insertion device for moving said jaws from their open positions to their closed positions, a handling case for holding said insertion device and lens until needed for lens implantation comprising a tray, and supporting means on the tray removably supporting said insertion device and said foldable lens in storage positions on the tray wherein (a) said jaws occupy their open positions, (b) said lens is positioned between the jaws with the lens in its normal unfolded configuration, and (c) said jaw closing means are accessible for closing said jaws about the lens in a manner to fold the lens to its compact folded configuration while said insertion device and lens remain on the tray, and wherein said insertion device and lens are removable from said tray with said jaws closed and gripping said lens in its folded configuration, said jaws have confronting inner concave sides which form a passage opening through said anterior and posterior ends of said insertion device when said jaws are closed, said lens when gripped in its folded configuration between said jaws is positioned within said passage and is ejectable anteriorly through said passage into the patient's eye after insertion of said anterior end of the device into the eye, and said jaws have confronting inner longitudinal edges with mating formations which interengage when the jaws are closed to coaxially align the jaws relative to one another.

* * * * *